(12) United States Patent  
Suzuki (10) Patent No.: US 11,992,368 B2  
(45) Date of Patent: May 28, 2024

(54) ENDOSCOPE CONNECTOR AND ENDOSCOPE

(71) Applicant: OLYMPUS CORPORATION, Tokyo (JP)

(72) Inventor: Norihisa Suzuki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 821 days.

(21) Appl. No.: 17/136,576

(22) Filed: Dec. 29, 2020

(65) Prior Publication Data

US 2021/0113183 A1    Apr. 22, 2021

Related U.S. Application Data

(63) Continuation of application No. PCT/JP2019/026384, filed on Jul. 2, 2019.

(30) Foreign Application Priority Data

Jul. 6, 2018 (JP) ................................ 2018-129298

(51) Int. Cl.  
*A61B 8/00* (2006.01)  
*A61B 8/12* (2006.01)

(52) U.S. Cl.  
CPC ................ *A61B 8/445* (2013.01); *A61B 8/12* (2013.01)

(58) Field of Classification Search  
CPC .................................. A61B 8/12; A61B 8/455  
See application file for complete search history.

(56) References Cited

U.S. PATENT DOCUMENTS

| 2012/0202385 | A1 | 8/2012 | Miyagi et al. |
| 2014/0094656 | A1 | 4/2014 | Matsukawa et al. |
| 2018/0054020 | A1 | 2/2018 | Tada et al. |
| 2018/0185004 | A1 | 7/2018 | Saiga |

FOREIGN PATENT DOCUMENTS

| EP | 2656779 A1 | 10/2013 |
| JP | 2010253267 A | * 11/2010 |
| JP | 2016-96039 A | 5/2016 |
| JP | 6197150 B2 | 9/2017 |
| WO | 2011/052408 A1 | 5/2011 |
| WO | 2013/114661 A1 | 8/2013 |
| WO | 2013/114703 A1 | 8/2013 |

OTHER PUBLICATIONS

International Search Report dated Sep. 24, 2019 issued in PCT/JP2019/026384.

* cited by examiner

*Primary Examiner* — Chao Sheng  
(74) *Attorney, Agent, or Firm* — Scully, Scott, Murphy & Presser, P.C.

(57) ABSTRACT

An endoscope connector includes: a metal member that is exposed to an outside of the endoscope connector and electrically connected to an endoscopic examination apparatus; an exterior member formed of a resin material; and an elastic member that is exposed to the outside, the elastic member being configured to close a gap between the exterior member and the metal member.

13 Claims, 7 Drawing Sheets

ENDOSCOPE CONNECTOR AND ENDOSCOPE

CROSS-REFERENCE TO RELATED APPLICATIONS

This application is a continuation of PCT international application No. PCT/JP2019/026384 filed on Jul. 2, 2019, which designates the United States, incorporated herein by reference, and which claims the benefit of priority from Japanese Patent Application No. 2018-129298, filed on Jul. 6, 2018, incorporated herein by reference.

BACKGROUND

1. Technical Field

The present disclosure relates to an endoscope connector and an endoscope.

2. Related Art

In the related art, there has been known an endoscope system in which an endoscope inserted into a subject to capture an object image in the subject is connected to an endoscopic examination apparatus that processes an image signal obtained by the imaging by using an endoscope connector (refer to JP 6197150 B, for example).

The endoscope connector described in JP 6197150 B includes: a metal member (first and second electrical contacts, or the like) that is electrically connected to an endoscopic examination apparatus; and an exterior member (exterior casing) formed of a resin material.

SUMMARY

In some embodiments, an endoscope connector includes: a metal member that is exposed to an outside of the endoscope connector and electrically connected to an endoscopic examination apparatus; an exterior member formed of a resin material; and an elastic member that is exposed to the outside, the elastic member being configured to close a gap between the exterior member and the metal member.

In some embodiments, an endoscope includes: an insertion portion that has a distal end and a proximal end and is provided with an ultrasound probe on a side of the distal end; an operating portion provided on a side of the proximal end of the insertion portion; and an endoscope connector including a metal member exposed to an outside of the endoscope connector and electrically connected to an endoscopic examination apparatus, an exterior member formed of a resin material having a linear expansion coefficient larger than a linear expansion coefficient of the metal member, and an elastic member that has an elastic modulus higher than an elastic modulus of the exterior member and is exposed to the outside, the elastic member being configured to close a gap between the exterior member and the metal member.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes for carrying out the disclosure (hereinafter referred to as embodiments) will be described with reference to the drawings. The disclosure is not limited to the embodiments described below. In the drawings, same reference signs are attached to the same components.

Schematic Configuration of Endoscope System

Figure 1:
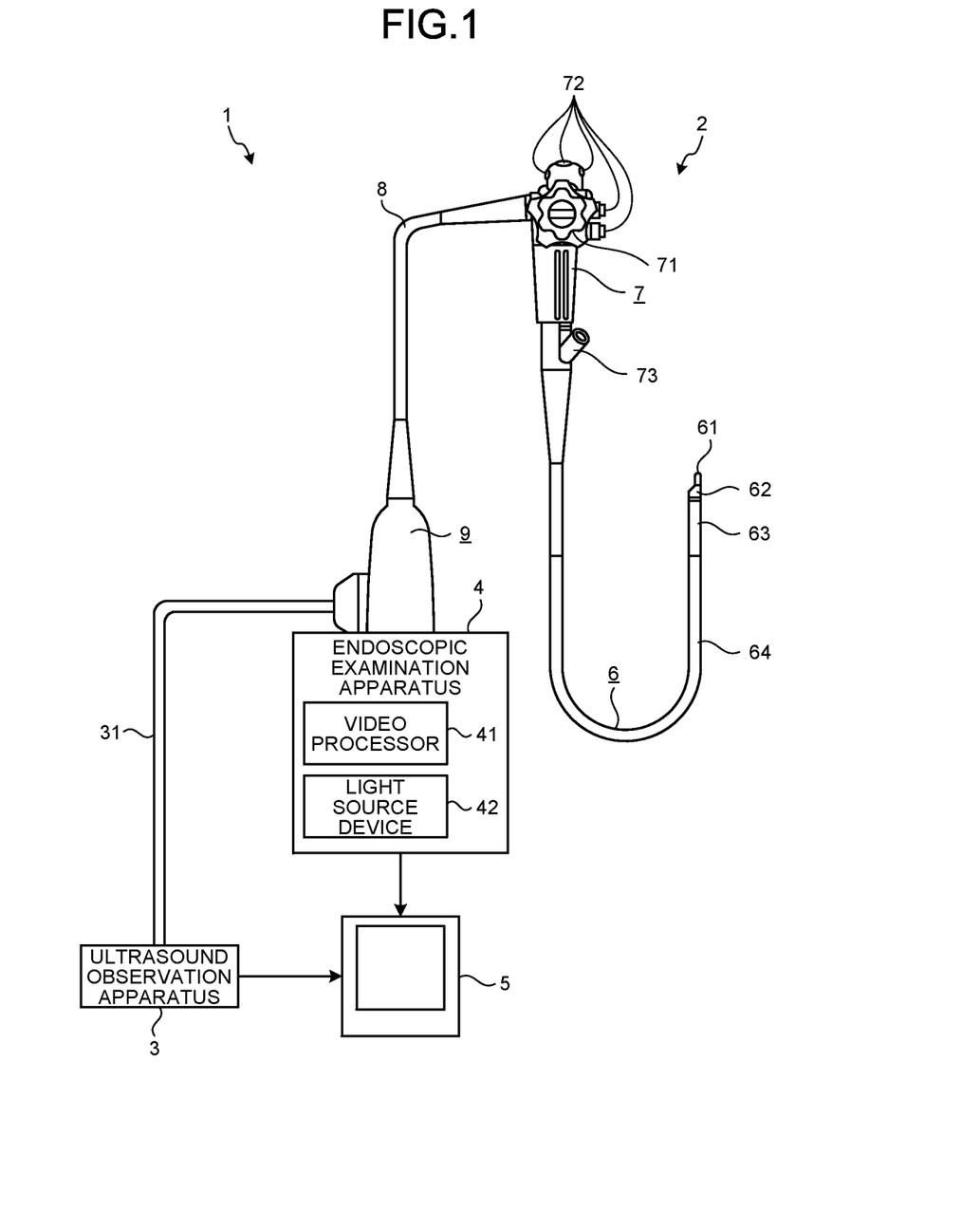
FIG. 1 is a diagram illustrating an endoscope system according to the present embodiment.

FIG. 1 is a diagram illustrating an endoscope system 1 according to the present embodiment.

An endoscope system 1 is a system for performing ultrasound diagnosis of internal portions of a subject such as a human by using an ultrasound endoscope. As illustrated in FIG. 1, the endoscope system 1 includes an ultrasound endoscope 2, an ultrasound observation apparatus 3, an endoscopic examination apparatus 4, and a display device 5.

The ultrasound endoscope 2 corresponds to the endoscope according to the disclosure. This ultrasound endoscope 2 is capable of being partially inserted into the subject, and has a function of transmitting an ultrasound pulse (acoustic pulse) toward a body wall in the subject and receiving an ultrasound echo reflected by the subject to output an echo signal, as well as a function of imaging an inside of the subject and outputting an image signal.

The detailed configuration of the ultrasound endoscope 2 will be described below.

The ultrasound observation apparatus 3 is electrically connected to the ultrasound endoscope 2 via an ultrasound cable 31 (FIG. 1), outputs a pulse signal to the ultrasound endoscope 2 via the ultrasound cable 31, while receiving an input of echo signals from the ultrasound endoscope 2. The ultrasound observation apparatus 3 subsequently performs predetermined processing on the echo signal and generates an ultrasound image.

The endoscopic examination apparatus 4 is detachably connected to an endoscope connector 9 (FIG. 1) (described below) of the ultrasound endoscope 2. As illustrated in FIG. 1, the endoscopic examination apparatus 4 includes a video processor 41 and a light source device 42.

The video processor 41 inputs an image signal from the ultrasound endoscope 2. The video processor 41 subsequently performs predetermined processing on the image signal and generates an endoscopic image.

The light source device 42 supplies illumination light for illuminating the inside of the subject to the ultrasound endoscope 2.

The display device 5 is formed with liquid crystal or organic electroluminescence (EL), and displays an ultrasound image generated by the ultrasound observation apparatus 3, an endoscopic image generated by the endoscopic examination apparatus 4, or the like.

Configuration of Ultrasound Endoscope

Next, the configuration of the ultrasound endoscope 2 will be described.

As illustrated in FIG. 1, the ultrasound endoscope 2 includes an insertion portion 6, an operating portion 7, a universal cord 8, and an endoscope connector 9.

In the following, in the description of the configuration of the insertion portion 6, a distal end side (distal end side in an insertion direction into the subject) of the insertion portion 6 will be simply described as the "distal end or distal end side", while a proximal end of the insertion portion 6 (operating portion 7 side) will be simply described as the "proximal end or proximal end side".

The insertion portion 6 is a portion to be inserted into the subject. As illustrated in FIG. 1, the insertion portion 6 includes an ultrasound probe 61 provided at a distal end, a rigid member 62 coupled to the proximal end side of the ultrasound probe 61, a bending portion 63 being a bendable portion coupled to the proximal end side of the rigid member 62, and a flexible tube 64 being a flexible portion coupled to the proximal end side of the bending portion 63.

Inside the insertion portion 6, the operating portion 7, the universal cord 8, and the endoscope connector 9, there are also provided a light guide (not illustrated) that transmits the illumination light supplied from the light source device 42, a transducer cable (not illustrated) that transmits the pulse signal and echo signal, and a signal cable (not illustrated) that transmits an image signal, as well as a pipeline (not illustrated) for circulating fluid.

Hereinafter, among the members 61 to 64 constituting the insertion portion 6, configurations of the ultrasound probe 61 and the rigid member 62 will be described.

The ultrasound probe 61 is a convex type ultrasound probe and includes a plurality of piezoelectric elements (not illustrated). The plurality of piezoelectric elements is regularly arranged to form a convex arc.

Here, the ultrasound probe 61 further includes an acoustic lens and a matching layer in addition to the above-described piezoelectric elements, and acquires an ultrasound echo that contributes to an ultrasound tomographic image inside the body wall in the subject. The pulse signal output from the ultrasound observation apparatus 3 passes through the ultrasound cable 31 and the above-described transducer cable, and thereafter is input to the ultrasound probe 61. Subsequently, the ultrasound probe 61 converts the pulse signal into an ultrasound pulse and transmits this ultrasound pulse into the subject. In addition, the ultrasound probe 61 converts the ultrasound echo reflected at an observation target site in the subject into an electrical echo signal. Subsequently, the echo signal passes through the above-described transducer cable and ultrasound cable 31 and is then input to the ultrasound observation apparatus 3.

Note that the ultrasound probe 61 is not limited to the convex type ultrasound probe, and a radial type ultrasound probe may be adopted.

The rigid member 62 is a rigid material member formed of a resin material or the like, and has a substantially columnar shape.

Here, although specific illustration is omitted, the rigid member 62 is provided with mounting holes, imaging holes, lighting holes, treatment tool channels, air/water feeding holes, or the like.

These mounting holes, imaging holes, lighting holes, treatment tool channels, and air/water feeding holes are holes that penetrate from the proximal end to the distal end of the rigid member 62, and specifically have the following functions.

The mounting hole is a hole into which the ultrasound probe 61 is mounted from the distal end side. The above-described transducer cable is inserted through the mounting hole and electrically connected to the ultrasound probe 61.

The imaging hole is a hole for acquiring an object image in the subject. Inside the imaging hole, there are provided an objective lens that gathers and focuses light for forming an object image, and an image sensor that captures an object image with the light focused with the objective lens. The image sensor outputs an image signal to the signal cable described above.

The lighting hole is a hole for directing illumination light into the subject. An emitting end of the light guide described above is inserted through the lighting hole, and the illumination light is emitted from the lighting hole.

The treatment tool channel is a hole for allowing protrusion of various treatment tools to the outside.

The air/water feeding hole is a hole that communicates with the above-described pipeline and blows a fluid flowing through the pipeline onto an outer surface of the above-described objective lens.

The operating portion 7 is coupled to the proximal end side of the insertion portion 6 and receives various types of operation from a doctor, or the like. As illustrated in FIG. 1, the operating portion 7 includes: a bending knob 71 for performing bending operation on the bending portion 63; and a plurality of operating members 72 for performing various types of operation. Furthermore, inside the flexible tube 64 and the bending portion 63, there is provided a treatment tool tube (not illustrated) communicating with the above-described treatment tool channel. The operating portion 7 is provided with a treatment tool insertion port 73 for inserting the treatment tool into the treatment tool tube.

The universal cord 8 is a cord extending from the operating portion 7 and for which the above-described light guide, transducer cable, signal cable, pipeline, or the like, are provided.

The endoscope connector 9 is a connector for connecting the ultrasound cable 31 and the universal cord 8, as well as being a connector to be inserted into the endoscopic examination apparatus 4 to connect the endoscopic examination apparatus 4 and the universal cord 8.

Configuration of Endoscope Connector

Next, the configuration of the endoscope connector 9 will be described with reference to FIGS. 2 to 7.

Figure 2:
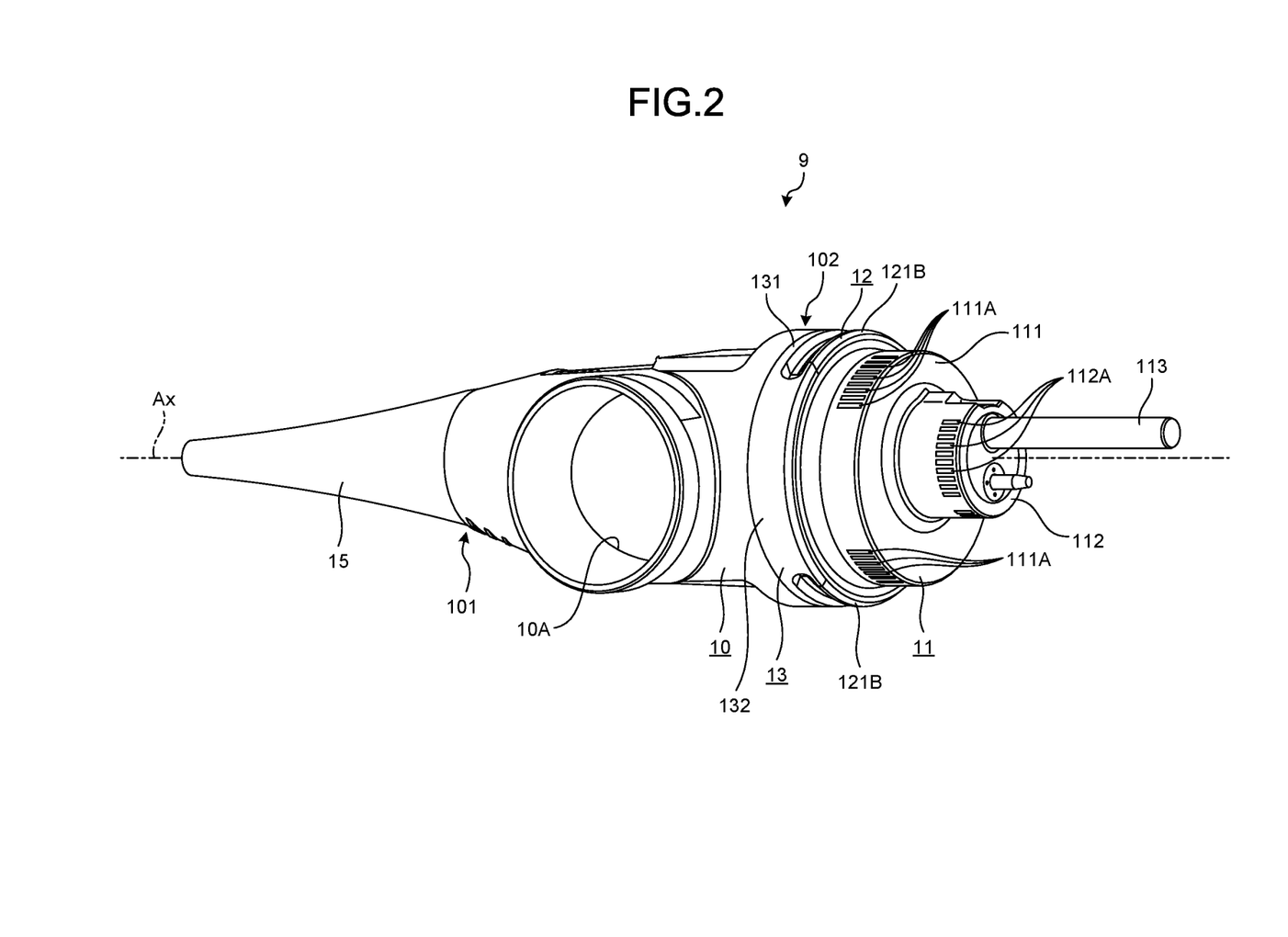
FIG. 2 is an overall perspective view of an endoscope connector.
Figure 3:
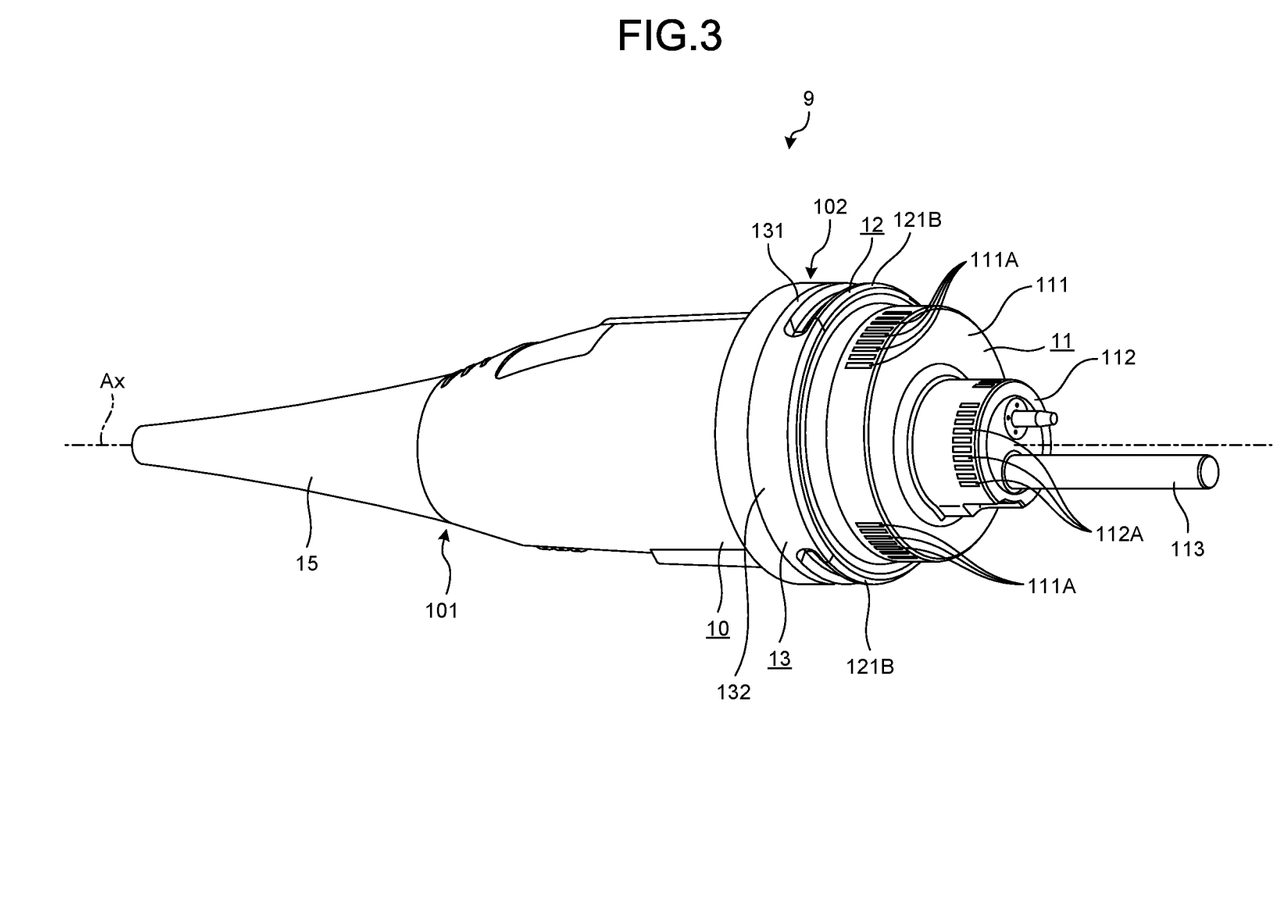
FIG. 3 is an overall perspective view of an endoscope connector.
Figure 4:
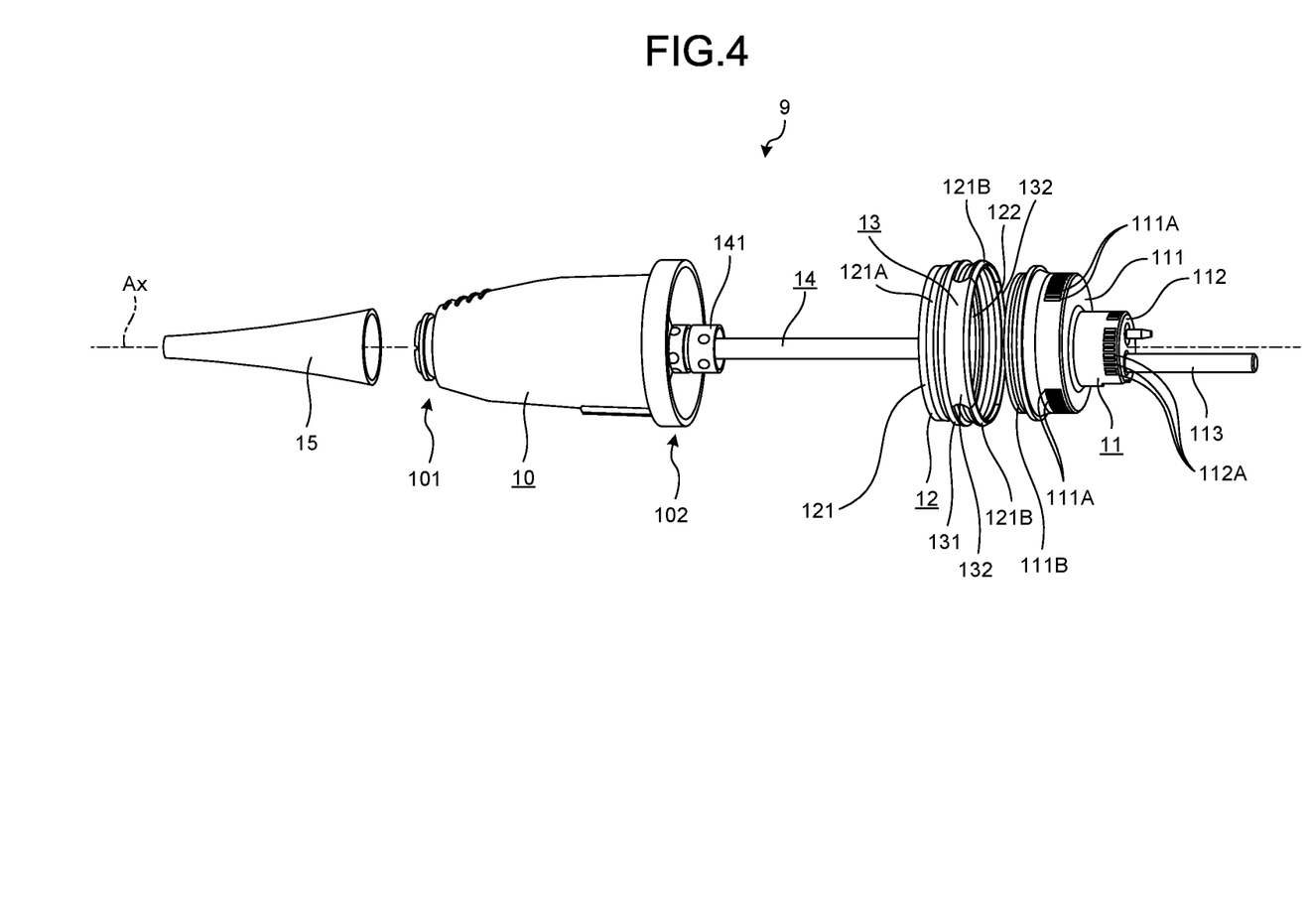
FIG. 4 is an exploded perspective view of an endoscope connector.
Figure 5:
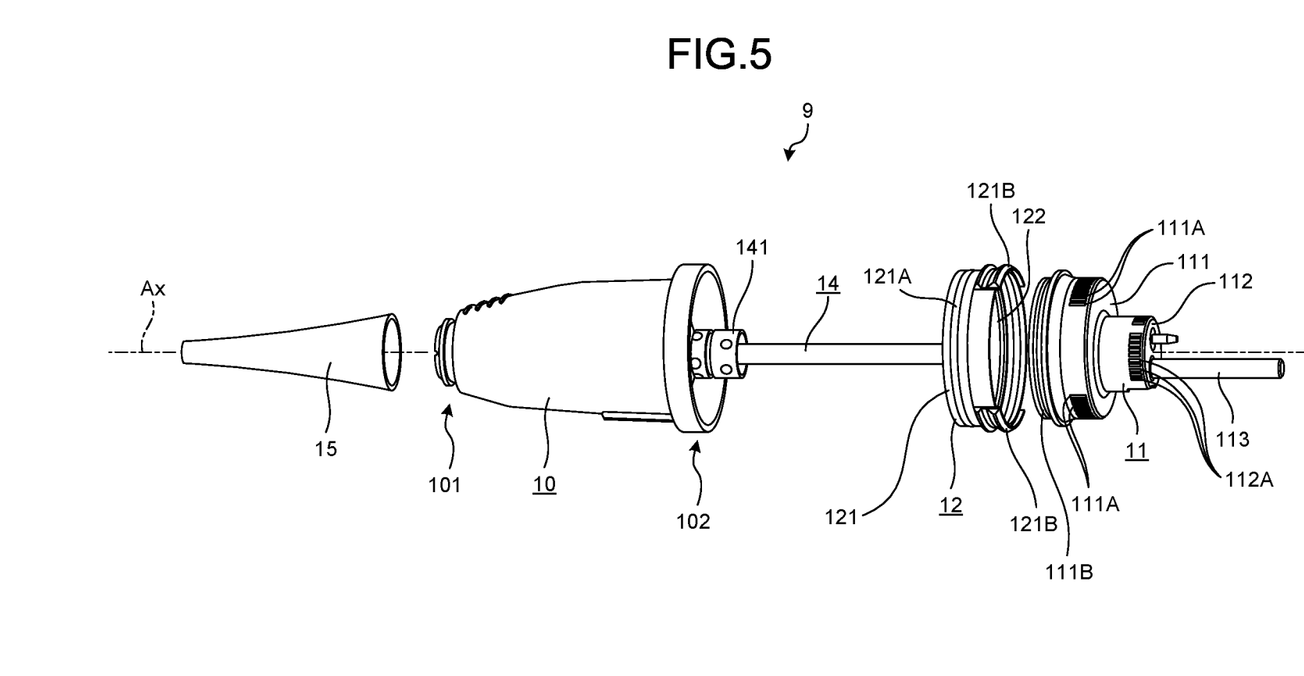
FIG. 5 is an exploded perspective view of an endoscope connector.
Figure 6:
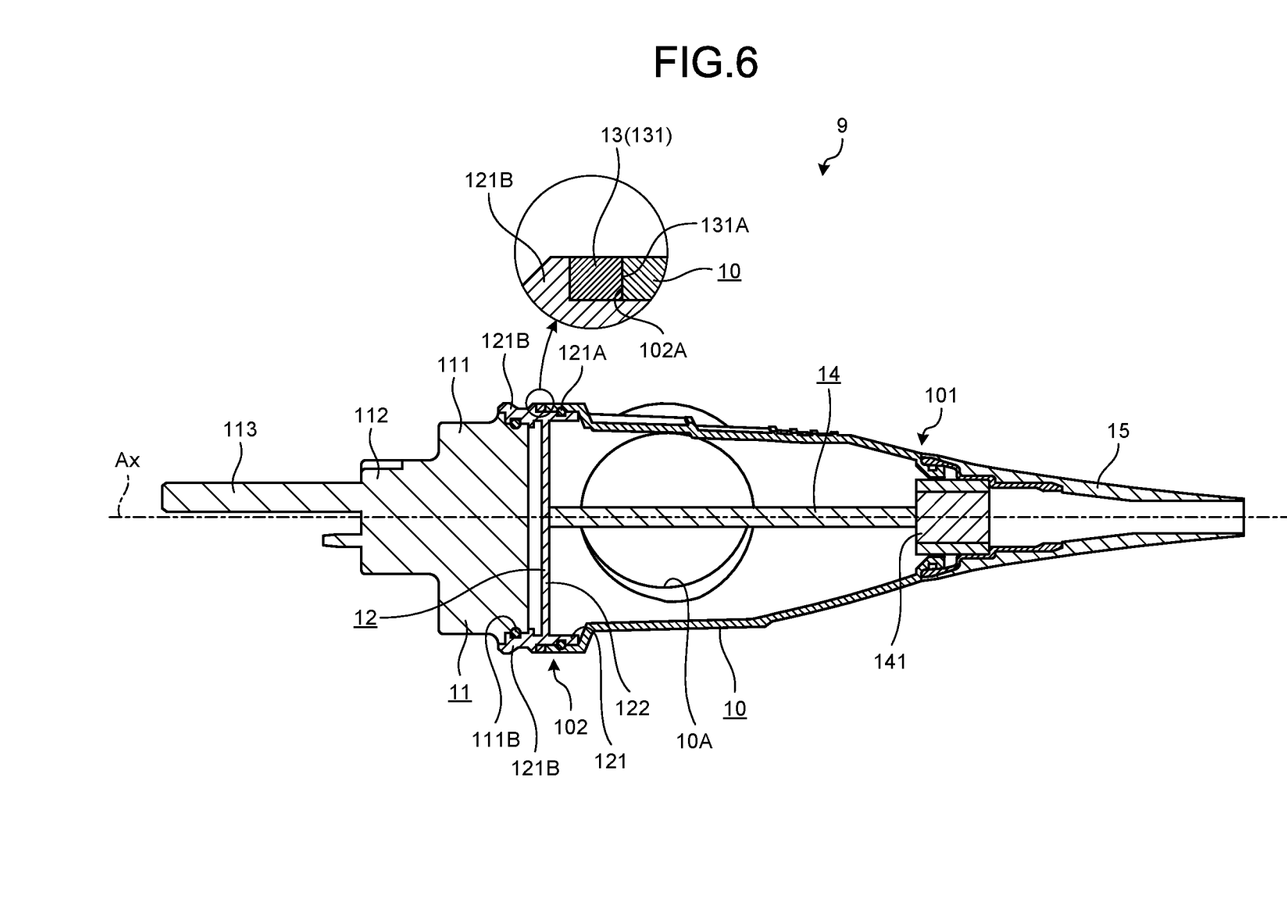
FIG. 6 is a cross-sectional view of an endoscope connector.
Figure 7:
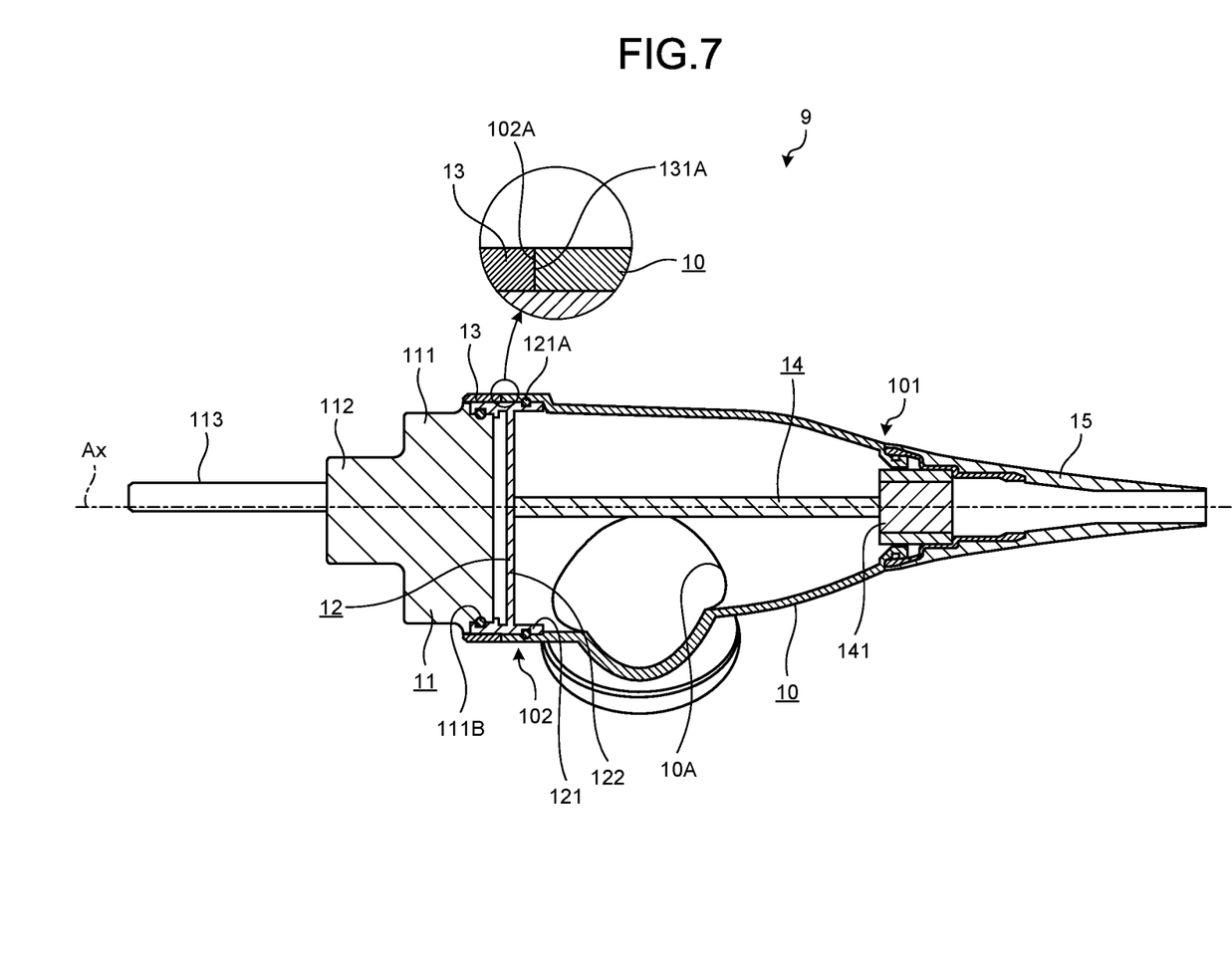
FIG. 7 is a cross-sectional view of an endoscope connector.

FIGS. 2 and 3 are overall perspective views of the endoscope connector 9. Specifically, FIGS. 2 and 3 are views of the endoscope connector 9 as seen from opposite directions. FIGS. 4 and 5 are exploded perspective views of the endoscope connector 9. For convenience of explanation, FIG. 5 omits illustration of an elastic member 13. FIGS. 6 and 7 are cross-sectional views of the endoscope connector 9. Specifically, FIG. 6 is a cross-sectional view of the endoscope connector 9 cut along a plane passing through a pair of locking units 121B, including a central axis Ax of an exterior member 10. FIG. 7 is a cross-sectional view of the endoscope connector 9 cut along a plane including the central axis Ax and avoiding the pair of locking units 121B.

In the following description of the configuration of the endoscope connector 9, the distal end side (right side (side where a plug unit 11 is provided) in FIG. 2) of the endoscope connector 9 will be simply referred to as the "distal end or distal end side", and the proximal end side (left side (the side where a holding member 15 is provided) in FIG. 2) of the endoscope connector 9 will be simply referred to as the "proximal end or proximal end side".

As illustrated in FIGS. 2 to 7, the endoscope connector 9 includes an exterior member 10, a plug unit 11, a metal member 12, and an elastic member 13 (FIGS. 2 to 4, 6, and 7), a connecting structure 14 (FIGS. 4 to 7) and a holding member 15.

The exterior member 10 is formed of a resin material having a linear expansion coefficient larger than that of the metal material. Examples of the resin material include polyphenylsulfone (PPSU) and polysulfone (PSU). As illustrated in FIGS. 2 to 7, the exterior member 10 has a substantially cylindrical shape. The universal cord 8 is inserted into the exterior member 10 from a proximal end portion 101. The proximal end portion 101 corresponds to the "other end of the exterior member" according to the disclosure.

Furthermore, on the outer circumferential surface of the exterior member 10, connector mounting holes 10A (FIGS. 2, 6, and 7) are provided to allow communication between the inside and outside of the exterior member 10. Although not illustrated for convenience of explanation, an ultrasound connector is mounted to the connector mounting hole 10A. The ultrasound connector is an electrical connector for electrically connecting the above-described transducer cable and the ultrasound cable 31.

When the endoscope connector 9 is inserted into the endoscopic examination apparatus 4, the plug unit 11 electrically connects to the video processor 41 and optically connects to the light source device 42. As illustrated in FIGS. 2 to 7, the plug unit 11 is attached to the distal end side of the metal member 12. The plug unit 11 includes first and second electrical connector units 111 and 112 and a light guide base 113.

The first electrical connector unit 111 is located on the most proximal end side of the plug unit 11 and has a columnar shape extending along the central axis Ax. On the distal end side of the outer circumferential surface of the first electrical connector unit 111, there is provide a plurality of first electrical contacts 111A (FIGS. 2 to 5) in a circumferential direction. Furthermore, on the proximal end side of the outer circumferential surface of the first electrical connector unit 111, an O-ring 111B (FIGS. 4 to 7) is attached.

The second electrical connector unit 112 is integrally formed on an end surface of the first electrical connector unit 111 on the distal end side, and is formed in a columnar shape having an outer dimension smaller than that of the first electrical connector unit 111. On the distal end side of the outer circumferential surface of the second electrical connector unit 112, there is provide a plurality of second electrical contacts 112A (FIGS. 2 to 5) in a circumferential direction.

The first and second electrical contacts 111A and 112A described above are electrically connected individually to signal lines in the signal cable described above. When the endoscope connector 9 is inserted into the endoscopic examination apparatus 4, the first and second electrical contacts 111A and 112A are electrically connected individually to the video processor 41. That is, the first and second electrical contacts 111A and 112A function as signal terminals.

The light guide base 113 is attached to an end surface on the distal end side of the second electrical connector unit 112, and protrudes from the end surface. Furthermore, an incident end of the light guide described above is optically connected to the light guide base 113 inside the endoscope connector 9. When the endoscope connector 9 is inserted into the endoscopic examination apparatus 4, the light guide base 113 optically connects the above-described light guide and the light source device 42.

The metal member 12 is provided between a distal end portion 102 and the plug unit 11 on the exterior member 10. The distal end portion 102 corresponds to "one end of the exterior member" according to the disclosure. As illustrated in FIGS. 4 to 7, the metal member 12 is a member integrally formed with an outer shell 121 and a plate body 122.

The outer shell 121 has a cylindrical shape extending along the central axis Ax.

In this outer shell 121, an O-ring 121A is attached to the proximal end side on the outer circumferential surface, as illustrated in FIGS. 4 to 7. This O-ring 121A corresponds to a watertight member according to the disclosure. The proximal end side of the outer shell 121 is fitted inside the distal end portion 102 of the exterior member 10 with the O-ring 121A interposed between the proximal end side and the exterior member 10. In the fitted state, the distal end side of the outer shell 121 is in a state of projecting from the distal end portion 102 to the distal end side. Furthermore, the proximal end side of the plug unit 11 is fitted inside the distal end side of the outer shell 121 with the O-ring 111B interposed between the distal end side and the outer shell 121.

Furthermore, on the outer shell 121, as illustrated in FIGS. 2 to 7, there is provided, on a distal end side on the outer circumferential surface, a pair of locking units 121B each of which protruding outward in a radial direction of the outer shell 121 and extending in an arc shape in the circumferential direction centered on the central axis Ax. The pair of locking units 121B is each provided at 180° rotationally symmetric positions about the central axis Ax and are exposed to the outside. When the endoscope connector 9 is inserted into the endoscopic examination apparatus 4, the pair of locking units 121B is locked to the endoscopic examination apparatus 4 so as to be mechanically connected to the endoscopic examination apparatus 4. Furthermore, the metal member 12 is electrically connected to a ground line (patient GND) in the signal cable described above. When the endoscope connector 9 is inserted into the endoscopic examination apparatus 4, the pair of locking units 121B is electrically connected individually to the video processor 41. That is, the metal member 12 functions as a ground terminal.

The plate body 122 is formed of a metal material and has a disk shape. The plate body 122 is integrally formed with the outer shell 121, and closes the inside of the outer shell 121. Each of signal lines in the above-described signal cable penetrates the plate body 122 from the proximal end side to the distal end side in a state of being electrically insulated from the plate body 122 (metal member 12) so as to be electrically connected to the first and second electrical contacts 111A and 112A.

The elastic member 13 is integrally formed with the distal end side of the outer circumferential surface of the outer shell 121 by insert molding, outsert molding, or lining. More specifically, the elastic member 13 includes an annular portion 131 and a pair of projections 132, as illustrated in FIG. 2 to 4, 6 or 7.

The annular portion 131 is located on the proximal end side with respect to the pair of locking units 121B, and extends all around the circumferential direction centered on the central axis Ax. In addition, as illustrated in FIG. 6 or 7, an end surface 131A on the proximal end side of the annular portion 131 comes into contact with the end surface 102A of the distal end portion 102 in a state where the proximal end side of the outer shell 121 is fitted inside the distal end portion 102 of the exterior member 10. Here, the end surfaces 131A and 102A that come into contact with each other are planes that are orthogonal to the central axis Ax and extend all around the circumferential direction centered on the central axis Ax. The end surfaces 131A and 102A correspond to the contact surfaces according to the disclosure.

The pair of projections 132 each project from the distal end side of the annular portion 131 so as to extend in an arc shape in the circumferential direction about the central axis Ax. The pair of projections 132 are continuous with the pair of locking units 121B in the circumferential direction centered on the central axis Ax. That is, the pair of projections 132 is each provided at 180° rotationally symmetric position about the central axis Ax, similarly to the pair of locking units 121B.

With the above-described configuration, the elastic member 13 is exposed to the outside and closes a gap between the distal end portion 102 of the exterior member 10 and the metal member 12 (the pair of locking units 121B).

In addition, the elastic member 13 is formed of a resin material (for example, silicone resin, fluororesin, or the like) having a higher elastic modulus than in the exterior member 10, as well as electrically insulating property, and excellent chemical resistance.

As illustrated in FIGS. 4 to 7, the connecting structure 14 is a structure extending along the central axis Ax, the distal end side of which being connected to the plate body 122 and inserted into the exterior member 10. On the proximal end side of the connecting structure 14, there is provided a screw portion 141 into which the holding member 15 is screwed. Although a specific illustration is omitted, there is provided a screw groove formed on an outer surface of the screw portion 141.

The holding member 15 has a substantially cylindrical shape extending along the central axis Ax, and into which the universal cord 8 is inserted. Although a specific illustration is omitted, a screw groove to be fitted to the screw groove of the screw portion 141 is formed on the distal end side of an inner circumferential surface of the holding member 15. That is, the holding member 15 is screwed into the screw portion 141. With the change in the screwed state, the holding member 15 makes a reciprocating movement with respect to the connecting structure 14 along the central axis Ax. In addition, by changing the screwed state of the holding member 15 with respect to the connecting structure 14 and moving the holding member 15 to the distal end side with respect to the connecting structure 14, the holding member 15 comes into contact with the proximal end portion 101 of the exterior member 10. That is, the exterior member 10 and the elastic member 13 are sandwiched between the metal member 12 and the holding member 15. Furthermore, the elastic member 13 is compressed in the direction along the central axis Ax.

The present embodiment described above achieves the following effects.

In the endoscope connector 9 according to the present embodiment, the elastic member 13 closes the gap between the exterior member 10 and the metal member 12. Therefore, with the elastic member 13, it is possible to absorb the difference in the expansion coefficient or the contraction rate between the exterior member 10 and the metal member 12 due to the heat or a chemical attack applied during the reprocess. This makes it possible to suppress an occurrence of a gap between the exterior member 10 and the metal member 12 or an occurrence of damage to the exterior member 10 due to the heat or chemical attack applied during the reprocess. That is, the influence of the reprocess can be suppressed. Furthermore, since it is possible to suppress the occurrence of the gap between the exterior member 10 and the metal member 12, no residuals such as contamination occurring at the use of the ultrasound endoscope 2 would stay in the gap, facilitating the reprocess.

Furthermore, since the elastic member 13 can suppress the influence of the reprocess, there will be no need to fill the adhesive between the exterior member 10 and the metal member 12. That is, the exterior member 10 can be easily removed from the metal member 12, and the member provided inside the exterior member 10 can be easily replaced.

Furthermore, in the endoscope connector 9 according to the present embodiment, the metal member 12 is provided at the distal end portion 102 of the exterior member 10 having a tubular shape. The elastic member 13 is provided between the distal end portion 102 and the metal member 12 (the pair of locking units 121B). This means that the metal member 12 is provided at the end of the exterior member 10. Accordingly, it is possible to remove the exterior member 10 from the metal member 12 more easily as compared with a configuration in which the metal member 12 is provided at a position other than the end.

Furthermore, in the endoscope connector 9 according to the present embodiment, the metal member 12 and the holding member 15 are individually connected to either end of the connecting structure 14, whereby the exterior member 10 and the elastic member 13 are sandwiched between the metal member 12 and the holding member 15.

In particular, the holding member 15 is screwed into the screw portion 141 of the connecting structure 14. With the change in the screwed state, the holding member 15 makes reciprocating movement with respect to the connecting structure 14 along the central axis Ax.

Therefore, the elastic member 13 can be appropriately compressed. That is, with the elastic member 13, it is possible to effectively absorb the difference in the expansion coefficient or the contraction rate between the exterior member 10 and the metal member 12 due to the heat or a chemical attack applied during the reprocess. Furthermore, with the presence of the O-ring 121A and the elastic member 13, it is possible to sufficiently ensure the watertightness between the distal end portion 102 and the metal member 12.

Furthermore, in the endoscope connector 9 according to the present embodiment, the end surfaces 102A and 131A that come into contact with each other in the exterior member 10 and the elastic member 13 are planes orthogonal to the central axis Ax and extending all around in the circumferential direction centered on the central axis Ax.

This can simplify the shapes of the end surfaces 102A and 131A and can facilitate the manufacturing of these parts, with an effect of improving the adhesion between the end surfaces 102A and 131A.

Furthermore, in the endoscope connector 9 according to the present embodiment, the elastic member 13 is formed of an electrically insulating material.

This makes it possible to sufficiently obtain the insulating property of the metal member 12 that functions as the ground terminal.

Furthermore, in the endoscope connector 9 according to the present embodiment, the elastic member 13 is formed of a material having chemical resistance.

This makes it possible to suppress the degradation of the elastic member 13 during the reprocess.

Furthermore, in the endoscope connector 9 according to the present embodiment, the pair of locking units 121B is locked to the endoscopic examination apparatus 4, thereby being mechanically connected to the endoscopic examination apparatus 4. That is, the metal member 12 has a function of mechanically connecting to the endoscopic examination apparatus 4 in addition to the function of the ground terminal.

Therefore, the number of parts can be reduced as compared with a case where a configuration for mechanically connecting to the endoscopic examination apparatus 4 is separately provided.

Other Embodiments

While the above is description of the modes for carrying out the disclosure, the disclosure should not be limited by only the embodiments described above.

In the above-described embodiment, the metal member 12 functions as a ground terminal. However, the disclosure is not limited to this, and it is allowable to adopt a configuration in which the metal member 12 functions as a signal terminal.

In the above-described embodiment, the endoscope system 1 has both a function of generating an ultrasound image and a function of generating an endoscopic image. The disclosure, however, is not limited to this, and the endoscope system 1 may have an endoscopic image generating function alone. That is, it is also allowable to have a configuration that has no ultrasound probe 61, the ultrasound observation apparatus 3, or the like.

In the above-described embodiment, the endoscope system 1 may be used in the industrial field and may be an endoscope system for observing the inside of a subject such as a mechanical structure.

According to the endoscope connector and the endoscope in the disclosure, there is an advantageous effect that the member provided inside the exterior member can be easily replaced while suppressing the influence of the reprocess.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope connector comprising:
a metal member that is exposed to an outside of the endoscope connector and electrically connected to an endoscopic examination apparatus;
an exterior member formed of a resin material; and
an elastic member that is exposed to the outside of the endoscope connector, the elastic member being configured to close a gap between the exterior member and the metal member.

2. The endoscope connector according to claim 1, wherein the metal member is provided at one end of the exterior member, and
the elastic member is provided between the one end of the exterior member and the metal member.

3. The endoscope connector according to claim 1, wherein the elastic member is formed of an electrically insulating material.

4. The endoscope connector according to claim 1, wherein the elastic member is formed of a material having chemical resistance.

5. The endoscope connector according to claim 1, wherein the metal member is configured to be locked to the endoscopic examination apparatus so as to be mechanically connected to the endoscopic examination apparatus.

6. The endoscope connector according to claim 1, wherein the metal member is a ground terminal that is electrically connected to the endoscopic examination apparatus.

7. The endoscope connector according to claim 1, wherein a watertight member is provided between the exterior member and the metal member.

8. The endoscope connector according to claim 1, wherein the resin material has a linear expansion coefficient larger than a linear expansion coefficient of the metal member, and
the elastic member has an elastic modulus higher than an elastic modulus of the exterior member.

9. The endoscope connector according to claim 1, wherein the exterior member has a tubular shape.

10. The endoscope connector according to claim 9, further comprising:
a connecting structure that is inserted inside the exterior member and has one end being connected to the metal member; and
a holding member that is attached to another end of the connecting structure, the holding member being configured to come in contact with another end of the exterior member,
wherein the exterior member and the elastic member are sandwiched between the metal member and the holding member.

11. The endoscope connector according to claim 10, wherein the holding member is screwed to the other end of the connecting structure, and is configured to make a reciprocating movement with respect to the connecting structure along a central axis of the exterior member in accordance with a change in a state of being screwed.

12. The endoscope connector according to claim 10, wherein a contact surface on which one end of the exterior member and the elastic member come into contact with each other is a plane that is orthogonal to a central axis of the exterior member and extends all around a circumferential direction centered on the central axis.

13. An endoscope comprising:
an insertion portion that has a distal end and a proximal end and is provided with an ultrasound probe on a side of the distal end;
an operating portion provided on a side of the proximal end of the insertion portion; and
an endoscope connector including a metal member exposed to an outside of the endoscope connector and electrically connected to an endoscopic examination apparatus, an exterior member formed of a resin material having a linear expansion coefficient larger than a linear expansion coefficient of the metal member, and an elastic member that has an elastic modulus higher than an elastic modulus of the exterior member and is exposed to the outside of the endoscope connector, the elastic member being configured to close a gap between the exterior member and the metal member.

* * * * *